United States Patent
Ojha et al.

(10) Patent No.: US 10,124,190 B2
(45) Date of Patent: Nov. 13, 2018

(54) RADIATION THERAPY PLANNING AND FOLLOW-UP SYSTEM WITH LARGE BORE NUCLEAR AND MAGNETIC RESONANCE IMAGING OR LARGE BORE CT AND MAGNETIC RESONANCE IMAGING

(75) Inventors: Navdeep Ojha, Mayfield Village, OH (US); Michael Andrew Morich, Mentor, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1130 days.

(21) Appl. No.: 13/993,424

(22) PCT Filed: Dec. 13, 2011

(86) PCT No.: PCT/IB2011/055637
§ 371 (c)(1),
(2), (4) Date: Jun. 12, 2013

(87) PCT Pub. No.: WO2012/080948
PCT Pub. Date: Jun. 21, 2012

(65) Prior Publication Data
US 2013/0267830 A1    Oct. 10, 2013

Related U.S. Application Data

(60) Provisional application No. 61/423,621, filed on Dec. 16, 2010.

(51) Int. Cl.
*A61B 5/00*    (2006.01)
*A61N 5/10*    (2006.01)
(Continued)

(52) U.S. Cl.
CPC .......... *A61N 5/1039* (2013.01); *A61B 5/0035* (2013.01); *A61B 5/055* (2013.01);
(Continued)

(58) Field of Classification Search
CPC ..... A61B 6/032; A61B 6/4417; A61B 6/5235; A61N 5/1049
See application file for complete search history.

(56) References Cited

U.S. PATENT DOCUMENTS 5,003,264 A * 3/1991 Koizumi et al. .............. 324/309
5,023,554 A * 6/1991 Cho .................... G01R 33/3806
324/309
(Continued)

FOREIGN PATENT DOCUMENTS

JP    S6349140    3/1988
JP    3502658    6/1991
(Continued)

OTHER PUBLICATIONS

B., Pichler, H. Wehrl, A., Kolb, M. Judenhofer, "PET/MRI: The Next Genreation of Multi-Modaltiy Imaging?", Semin Nucl MEd, 38(3), 2008.*
(Continued)

*Primary Examiner* — Joanne Hoffman (57) ABSTRACT

A radiation therapy planning and follow-up system (10) includes an MR scanner (12) with a first bore (16) which defines an MR imaging region (18) and a functional scanner (26), e.g., a nuclear imaging scanner, or a CT scanner with a second bore (30) which defines a nuclear or CT imaging region (36). The first and second bores (16,30) have a diameter of at least 70 cm, and preferably 80-85 cm. A radiation therapy type couch (90) moves linearly through the MR imaging region (18) along an MR longitudinal axis and the nuclear or CT imaging region (36) along a nuclear or CT longitudinal axis which is aligned with the MR longitudinal axis. The couch positions a subject sequentially in the MR and nuclear or CT imaging regions (18, 36). A fusion processor combines an image representation generated from data collection in the MR imaging region (18) and an image
(Continued)

representation generated from data collection in the nuclear or CT imaging region (36) into a composite image representation and a planning processor (112) generates a radiation therapy treatment plan according to the composite image.

12 Claims, 4 Drawing Sheets

(51) Int. Cl.
*A61B 5/055* (2006.01)
*G01R 33/48* (2006.01)
*A61B 6/03* (2006.01)
*A61B 6/00* (2006.01)

(52) U.S. Cl.
CPC ............ *A61B 5/0555* (2013.01); *A61B 6/032* (2013.01); *A61B 6/037* (2013.01); *A61B 6/4417* (2013.01); *A61B 6/5247* (2013.01); *A61N 5/1071* (2013.01); *G01R 33/481* (2013.01); *G01R 33/4808* (2013.01); *G01R 33/4812* (2013.01); *A61N 2005/1052* (2013.01); *A61N 2005/1055* (2013.01); *A61N 2005/1061* (2013.01)

(56) References Cited

U.S. PATENT DOCUMENTS

| | | | |
|---|---|---|---|
| 5,178,146 A | 1/1993 | Giese | |
| 6,205,347 B1* | 3/2001 | Morgan et al. | 600/407 |
| 6,416,219 B1* | 7/2002 | Pflaum et al. | 378/209 |
| 8,791,435 B2 | 7/2014 | Balakin | |
| 9,687,200 B2* | 6/2017 | Maurer, Jr. | A61B 6/032 |
| 2002/0065461 A1* | 5/2002 | Cosman | A61B 6/5247 |
| | | | 600/426 |
| 2003/0048868 A1* | 3/2003 | Bailey et al. | 378/65 |
| 2003/0128801 A1* | 7/2003 | Eisenberg et al. | 378/19 |
| 2003/0181804 A1* | 9/2003 | Gagnon | G06F 19/3487 |
| | | | 600/410 |
| 2004/0022351 A1* | 2/2004 | Lacey et al. | 378/19 |
| 2005/0152492 A1 | 7/2005 | Yakubovsky et al. | |
| 2005/0160529 A1* | 7/2005 | Tybinkowski et al. | 5/601 |
| 2005/0197564 A1* | 9/2005 | Dempsey | A61B 5/055 |
| | | | 600/411 |
| 2006/0052685 A1* | 3/2006 | Cho | G01R 33/20 |
| | | | 600/407 |
| 2006/0124855 A1* | 6/2006 | Gagnon | A61B 6/037 |
| | | | 250/370.09 |
| 2007/0167806 A1* | 7/2007 | Wood et al. | 600/459 |
| 2007/0269008 A1* | 11/2007 | Pomper | 378/65 |
| 2008/0061241 A1 | 3/2008 | Rietzel | |
| 2008/0169812 A1* | 7/2008 | Ladebeck et al. | 324/318 |
| 2008/0214927 A1* | 9/2008 | Cherry et al. | 600/411 |
| 2008/0265887 A1* | 10/2008 | Linz et al. | 324/318 |
| 2008/0312526 A1* | 12/2008 | Gagnon | G01R 33/28 |
| | | | 600/411 |
| 2009/0003522 A1* | 1/2009 | Chien | A61N 5/1049 |
| | | | 378/65 |
| 2009/0209844 A1* | 8/2009 | Gagnon | A61B 5/0555 |
| | | | 600/411 |
| 2009/0216110 A1* | 8/2009 | Piron | G01R 33/36 |
| | | | 600/415 |
| 2009/0246145 A1* | 10/2009 | Small | A61K 31/47 |
| | | | 424/9.361 |
| 2009/0262894 A1* | 10/2009 | Shukla et al. | 378/65 |
| 2010/0021112 A1* | 1/2010 | Moriarty | G02B 6/3855 |
| | | | 385/89 |
| 2010/0128839 A1* | 5/2010 | Partain | A61N 5/1048 |
| | | | 378/4 |
| 2010/0198112 A1 | 8/2010 | Maad | |
| 2013/0137964 A1* | 5/2013 | Schellenberg | A61B 5/0555 |
| | | | 600/411 |

FOREIGN PATENT DOCUMENTS

| | | |
|---|---|---|
| JP | 2002522129 | 7/2002 |
| JP | 2009540882 | 11/2009 |
| JP | 2010508079 | 3/2010 |
| WO | 03032836 A1 | 4/2003 |
| WO | WO 03032836 A2 * | 4/2003 |
| WO | 2007127970 A2 | 11/2007 |
| WO | 2010095063 A1 | 8/2010 |

OTHER PUBLICATIONS

Image-Guided Radiation Therapy, Wikipedia http://en.wikipedia.org/wiki/Image-guided_radiation_therapy downloaded Sep. 21, 2010.
Pichler, et al "PET/MRI: The Next Generation of Multi-Modality Imaging?", Semin Nucl Med. May 2008; 38(3) 199-208.
sensL Advertisement http://sensl.com/our-appplictions/nuclear-medicine/petmri/ downloaded Sep. 21, 2010.
Mutic, "Use of CT and PET in Radiation Therapy", http://www.aapm.org/meetings/02AM/pdf/8342-98194.pdf downloaded Sep. 21, 2010.
Brunt, J.N.H.; Computed Tomography-Magnetic Resonance Image Registration in Radiotherapy Treatment Planning; 2010; Clinical Oncology; 22:688-697.
Zaidi, H., et al.; Molecular PET/CT Imaging-Guided Radiation Therapy Treatment Planning; 2009; Acad. Radiol.; 16:1108-1133.

* cited by examiner

RADIATION THERAPY PLANNING AND FOLLOW-UP SYSTEM WITH LARGE BORE NUCLEAR AND MAGNETIC RESONANCE IMAGING OR LARGE BORE CT AND MAGNETIC RESONANCE IMAGING

CROSS REFERENCE TO RELATED APPLICATIONS

This application is a national filing of PCT application Ser. No. PCT/IB2011/055637, filed Dec. 13, 2011, published as WO 2012/080948 A1 on Jun. 21, 2012, which claims the benefit of U.S. provisional application Ser. No. 61/423,621 filed Dec. 16, 2010, which is incorporated herein by reference.

The present application relates to image guided radiation therapy planning. It finds particular application in conjunction with multi-modality radiation therapy planning.

Radiation therapy is a common therapeutic technique in oncology in which a dose or series of doses of high energy gamma ($\gamma$) radiation, particle beam, or other radiation is delivered to a patient's body or targeted region of a patient's body to achieve a therapeutic effect, e.g. eradicate cancerous tissue. The radiation therapy session(s) are planned prior to radiation treatment based on one or more planning volumetric images which aim to define the anatomical boundaries of the tumor and surrounding tissues in order to determine radiation beam parameters and dose distribution. Computed tomography (CT) scanners are typically employed in radiation therapy planning (RTP) because the imaging bore has sufficient size to accommodate the equivalent of larger/flat radiation therapy couches and average size or larger than average size patients with immobilization devices. Also, the CT data so acquired provides directly the attenuation properties of the tissue which is useful for RTP. RTP couches are carefully designed flat supports that ensure the patient is treated in the same position as imaged. One problem with CT imaging for RTP is that the patient is subjected to additional ionizing radiation which causes concern for additional long term adverse side effects such as cancer (which is in many cases the very thing being treated). In addition, CT fails to provide the requisite image quality for all soft-tissue regions of the body.

Positron emission tomography (PET) has been recently introduced as a viable imaging modality for cancer detection, including metastatic spread. When fused with other data, such as CT, PET provides additional tumor functional information for radiation therapy planning and monitoring. In PET scans, a patient is administered a radiopharmaceutical, in which the radioactive decay events of the radiopharmaceutical produce positrons. Each positron interacts with an electron over a short range to produce a positron-electron annihilation event that emits two oppositely directed gamma rays. Using coincidence detection circuitry, a ring array of radiation detectors surrounding the patient detects the coincident oppositely directed gamma ray events which correspond to the annihilation event. A line of response (LOR) connecting the two coincident detections contains the position of the annihilation event. The lines of response are analogous to projection data and are reconstructed to produce a two- or three-dimensional image. PET focuses on regions of high metabolic activity, such as neoplastic cancerous tissue and therefore helps to differentiate malignant tumors from benign tumors, hypoxic regions, characterize tumor recurrence, and radiation necrosis.

PET has shown potential to improve staging, prognosis, planning, and follow-up monitoring. However, a few limitations of PET include limited spatial resolution and a lack of additional anatomic detail beyond tissue where high tracer accumulation occurs. PET is generally poor at delineating anatomical detail and therefore has difficulty locating a tumor relative to other patient anatomy. Multi-modality PET-CT systems exists for radiation therapy planning but, as mentioned above, this arrangement will still subject the patient to additional harmful ionizing radiation from the CT scanning employed. Magnetic resonance imaging (MRI) and spectroscopy (MRS) offer potential as a replacement for anatomical imaging in RTP. In MR scans, the nuclear spins of the body tissue to be examined are aligned by a static main magnetic field $B_0$ and are excited by transverse magnetic fields $B_1$ oscillating in the radio frequency (RF) band. The resulting relaxation signals are exposed to gradient magnetic fields to localize the resultant resonance. The relaxation signals are received and reconstructed in a known manner into a single or multiple dimension image. MRI has superior soft tissue imaging while MRS is capable of characterizing tissue metabolism which can provide information regarding angiogenesis, cell proliferation, and apoptosis in the region of interest. However, magnetic resonance systems are limited by their bore size which cannot comfortably accommodate the larger than average size patients and larger RTP couch/flat tabletop. Furthermore, in certain immobilization/fixation situations additional bore space (>70 cm) is beneficial and currently does not exist for MR systems.

Accuracy of image registration between imaging modalities is an important feature for RTP and therefore both scans must preferably be performed in the same session to avoid patient movement and misregistration errors. Discrepancies between combined image representations can have a significant impact on treatment evaluation tools such as dose volume histogram, tumor control probability, normal tissue complication probability, and conformality index. Therefore, a need exists for a PET-MRI multi-modality radiation therapy planning system with a bore large enough to comfortably accommodate the RTP couch/flat tabletop, larger than average size patient, and immobilization devices to perform scans in a single imaging session with improved workflow.

The present application provides a new and improved method and system which overcomes the above-referenced problems and others.

In accordance with one aspect, a radiation therapy planning (RTP) system is presented. The RTP system includes a magnetic resonance (MR) system with a first bore which defines an MR imaging region which receives a subject along an MR longitudinal axis. The first bore has a diameter of at least 70 cm, and in a preferred embodiment is 85 cm. The RTP system includes a nuclear imaging scanner with a second bore which defines a nuclear imaging region which receives the subject along a nuclear longitudinal axis which is aligned with the MR longitudinal axis. The second has a diameter of at least 70 cm, and in a preferred embodiment is 85 cm. The system includes a radiation therapy couch with flat tabletop which moves linearly through the MR and nuclear imaging regions which positions the subject sequentially in the MR and nuclear imaging region. The flat tabletop material is compatible with both MR and PET imaging procedures.

In accordance with another aspect, a method for generating or updating a radiation therapy plan is presented. The method includes positioning a subject supported by a radiation therapy couch in one of an MR imaging region of an MR scanner and a nuclear imaging region of a nuclear scanner. An MR or nuclear image representation of a target volume is acquired and the target volume is localized relative to the corresponding imaging region. The localized target volume is registered to the radiation therapy couch and an expected coordinate position of the patient is determined relative to the radiation therapy couch. The subject is re-positioned linearly from one of the MR imaging region and nuclear imaging region to the other imaging region of one of the nuclear scanner and MR scanner which shares a common longitudinal axis therewith. An image representation of the target volume is acquired with the other one of the nuclear and MR scanners. The acquired MR and nuclear image representations are combined into a combined image representation. A radiation therapy plan is generated, or updated, according to the one of the combined, MR, and nuclear image representations.

One advantage resides in an improved workflow.

Another advantage is that ionizing radiation exposure during radiation therapy planning is reduced.

Another advantage is that the radiation therapy plan will be improved by the addition of soft-tissue contrast from the MR images.

Still further advantages of the present invention will be appreciated by those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
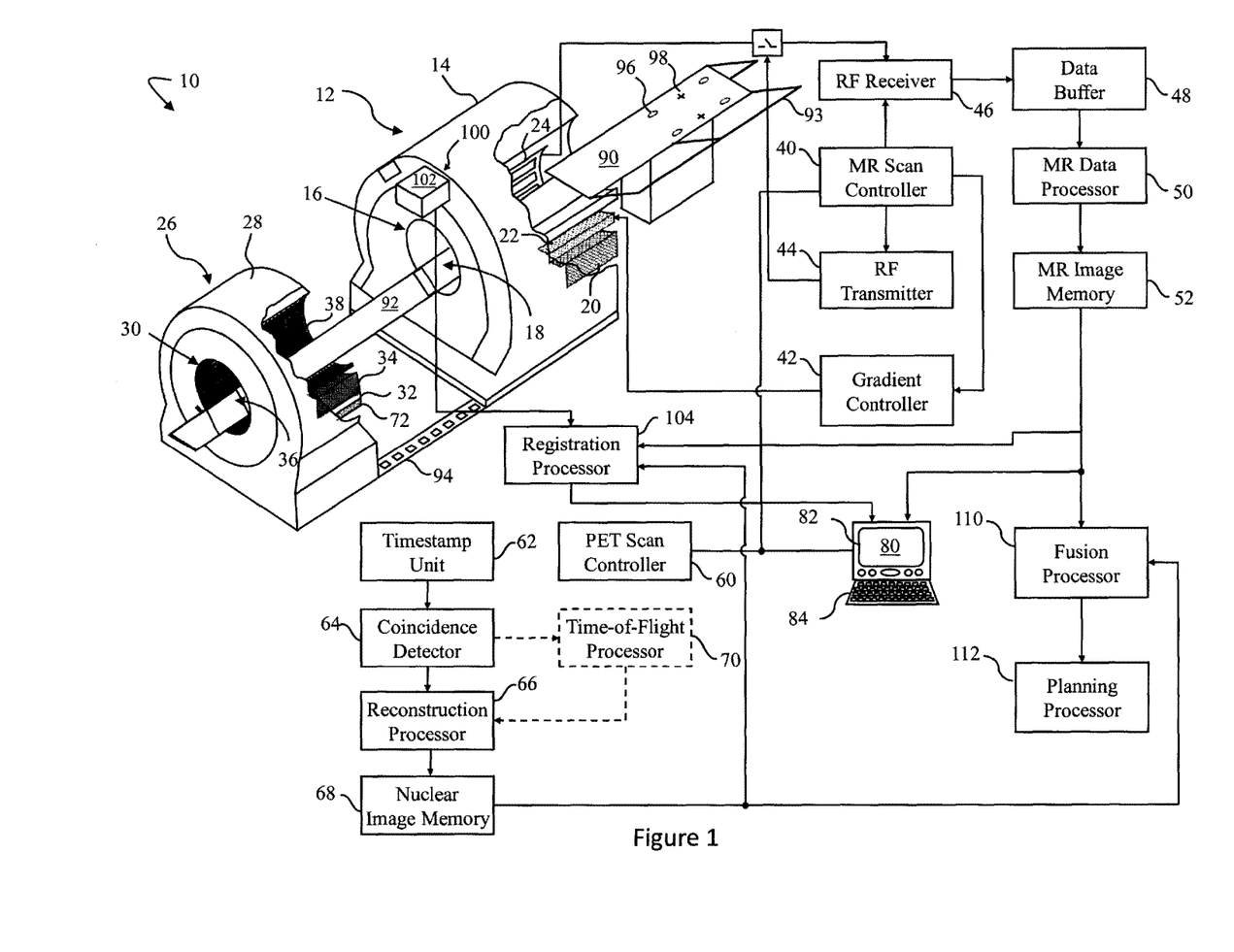
FIG. 1 is a diagrammatic illustration of a multiple modality radiation therapy planning system.

With reference to FIG. 1, a radiation therapy planning (RTP) system 10 is capable of magnetic resonance imaging and/or spectroscopy and a second imaging modality such as nuclear imaging, e.g. PET, SPECT, or computed tomography (CT) imaging. The RTP system 10 includes an anatomical imaging system, in the illustrated embodiment a large bore anatomical scanner 12, such as a magnetic resonance scanner, housed within a first gantry 14. A first patient receiving bore 16 defines a first or MR examination region 18 of the MR scanner 12. The patient receiving bore 16 has a diameter of at least 70 cm. However, larger bore diameters, such as 85 cm, are also contemplated. Larger bore MR scanners can be realized by increasing the clear bore of the superconducting magnet, and increasing the diameter of RF body coil and gradient coil components within the bore. The reduced efficiency of RF body coil (for transmit function) and gradient coil components can be offset somewhat by use of increased RF amplifier power and gradient amplifier power. The MR scanner includes a main magnet 20 which generates a temporally stable and spatially uniform $B_0$ field through the first examination region 18. Gradient magnetic field coils 22 disposed adjacent the main magnet serve to generate magnetic field gradients along selected axes relative to the $B_0$ magnetic field for spatially encoding magnetic resonance signals, for producing magnetization-spoiling field gradients, or the like. The magnetic field gradient coil 22 may include coil segments configured to produce magnetic field gradients in three orthogonal directions, typically longitudinal or z, transverse or x, and vertical or y-directions. The gradient coils maybe recessed into the main magnet to accommodate the increased bore diameter.

A radio-frequency (RF) coil assembly 24, such as a whole-body radio frequency coil, is disposed adjacent the examination region. The RF coil assembly generates radio frequency $B_1$ pulses for exciting magnetic resonance in the aligned dipoles of the subject. The radio frequency coil assembly 24 also serves to detect magnetic resonance signals emanating from the imaging region within a field-of-view (FOV) having a cross-sectional diameter of at least 55 cm. Receive-only RF coils may also be used for detection of the magnetic resonance signals. A larger FOV of approximately 60-65 cm can be achieved with the larger 85 cm bore. Optional localized iron boosters are incorporated into the RF coil assembly 24 to achieve the larger cross-sectional FOV without truncating the axial FOV. In this arrangement, the axial FOV is increased proportionally to the increase of the cross-sectional FOV, by magnet design, or optionally the axial FOV is maintained to be similar to smaller bore (e.g., 60 cm bore) MR systems to create an oblate spherical or ellipsoidal imaging volume. In large bore MR systems, typically there are no provisions for extending the axial FOV beyond that of a conventional 60 cm bore system.

The second imaging system, in the illustrated embodiment a functional scanner 26, such as a PET scanner, is housed within a second gantry 28 which defines a second patient receiving bore 30. The patient receiving bore 30 has a diameter of at least 70 cm. However, larger bore diameters, such as 85 cm, are also contemplated. It should be appreciated that a CT scanner, SPECT scanner, or the like, is also contemplated. A stationary ring of radiation detectors, such as a layer of optical detectors 32 optically coupled to a scintillator layer 34, is arranged around the bore 30 to define a second or PET examination region 36. An RF shield 38 is optionally disposed on the face of the optical detector 32 and scintillator 34 assembly and, in some embodiments, extends down the front and rear ends of the detector assembly. The RF shield 38 shields RF noise emanating from the PET scanner that may interfere with MR scanning Where the PET (or SPECT) scanner utilizes conventional photo multiplier tubes (PMTs) as optical detectors, they would incorporate magnetic shielding material to reduce effects of the fringe magnetic field of the MR system on the PMTs. Where solid state detectors are used magnetic shielding can be eliminated (but RF shielding would still be utilized). The RF shielding is also beneficial in the event the leakage RF field from RF pulses of the MR scanner 12 could excite or interfere with scintillators associated electronics. Therefore, the RF shield 38 also acts to reduce the RF interference originating from the optical detectors 32 and associated circuitry. The scintillator layer 34 is constantly emitting optical radiation which triggers an electrical response from the optical detectors. This electrical response generates RF interference which can adversely affect the MR signal to noise ratio. In a SPECT scanner, the detectors 32 are incorporated into individual heads, which are mounted for rotation about the second bore 30 and radial movement relative to the subject.

To acquire magnetic resonance data of a subject, the subject is positioned inside the MR examination region 18, preferably at or near an isocenter of the main magnetic field. A scan controller 40 controls a gradient controller 42 which causes the gradient coils 22 to apply the selected magnetic field gradient pulses across the imaging region, as may be appropriate to a selected magnetic resonance imaging or spectroscopy sequence. The scan controller 40 controls an RF transmitter 44 which causes the RF coil assembly 24 to generate magnetic resonance excitation and manipulation $B_1$ pulses. The scan controller also controls one or more RF receivers 46 which are connected to the RF coil assembly 24 to receive the generated magnetic resonance signals therefrom. The received data from the receivers 46 is temporarily stored in a data buffer 48 and processed by a MR data processor 50. The MR data processor 50 can perform various functions as are known in the art, including image reconstruction (MRI), magnetic resonance spectroscopy (MRS), and the like. Reconstructed magnetic resonance images, spectroscopy readouts, and other processed MR data are stored in an MR image memory 52.

To acquire nuclear imaging data, the patient is positioned in the PET examination region 36. The PET scanner 26 is operated by a PET scan controller 60 to perform selected imaging sequences of the selected target area. Typically, an object or patient to be imaged is injected with one or more radiopharmaceutical or radioisotope tracers then placed in the PET examination region 36. Examples of such tracers for PET are 18F-FDG, C-11, and for SPECT are Tc-99m, Ga67, and In-111. For SPECT tracers, gamma radiation is produced directly by the tracer. For PET, the presence of the tracer within the object produces emission radiation from the object. Radiation events are detected by the scintillator detectors 34 around the examination region 36. A time stamp is associated with each detected radiation event by a time stamp unit 62. A coincidence detector 64 determines coincident pairs of γ rays and the line of responses (LOR) defined by each coincident pair of γ rays based on differences in detection time of the coincidence pairs and the known diameter of the field of view. A reconstruction processor 66 reconstructs all the LORs into an image representation which is stored in a functional image memory 68. Optionally, a time-of-flight processor 70 localizes each radiation event by deriving time-of-flight information from the timestamps for each LOR.

In one embodiment, the patient is positioned first in the nuclear scanner 26 and imaged. After the nuclear image data is acquired, selected components of the nuclear scanner 26 are powered down, and in the case of PMTs the applied bias voltage is temporarily lowered to reduce/stop the emission of RF signals that could interfere with the MR scanner 12 during image acquisition. The patient support is translated into the MR examination region 18 and the MR scanner 12 acquires MR imaging data, including data for attenuation correction of the PET data, for reconstruction. Once the MR data acquisition is complete, the selected components of the nuclear scanner 26 are powered up. By the time the current patient leaves the examination room and the next patient arrives and is prepared for imaging, the nuclear scanner 26 is fully operational and ready for nuclear image data acquisition of the patient. If the nuclear detectors have not reached their nominal operating temperature, heating elements 72 can accommodate the process. In another embodiment, the optical detectors 32 and associated circuitry of the nuclear scanner 26 are selectively powered down during an MR procedure. To recommence normal operation of the PET scanner 26, a heating element 72 rapidly increases the optical detectors 32 temperature to a nominal operating temperature after a prolonged quiescent period or maintains a minimum operating temperature during the quiescent period. The nuclear scanner 26 can be placed in a quiescent mode which includes powering down or by reducing power supplied to the optical detectors 32 to reduce RF interference. After a quiescent period, the scanner is activated or placed in an active mode with the optional aid of the heating element 72 to acquire nuclear imaging data. The heating element 72 can be a resistive heating element, a warm air conduit, a fluid radiator, or the like. In another embodiment, the PET circuitry 60, 62, 64, 66, 68, 70 are disposed outside of the examination room to reduce RF interference. Alternatively or additionally, the MR scanner 12 can be placed in a quiescent (reduced RF noise) mode during the nuclear imaging procedure.

The diagnostic imaging system 10 includes a workstation or graphic user interface (GUI) 80 which includes a display device 82 and a user input device 84 which a clinician can use to select scanning sequences and protocols, display image data, and the like.

The two gantries 14, 28 are adjacent to one another in a linear arrangement and in close proximity to one another. The gantries 14, 28 share a common radiation therapy planning (RTP) couch 90 that translates along a longitudinal axis between the two examination regions 18, 36 along a patient support track or path 92. Optionally the couch is of a rotating design to accommodate rotation of the patient between PET and MR scanners, along with linear travel through each. A motor or other drive mechanism (not shown) provides the longitudinal movement and vertical adjustments of the support in the examination regions 18, 34. Optionally, the RTP couch 90 includes retractable rails 93, shown in the retracted position, to keep the patient on the couch during transit. In the illustrated embodiment, the second gantry 28 translates along a gantry track 94 to reduce the patient's transit time between the two imaging systems 12, 26. A closed arrangement between gantries reduces the likelihood of patient movement and misregistration errors. The gantries can be separated to reduce interference between the imaging modalities. For example, the optical detectors 32 of the PET scanner 26 emit RF signals which may interfere with resonance detection of the MR scanner 12. Also, the magnetic fringe field of the MR scanner reduces with distance from the scanner. In one embodiment, the gantries 14, 28 can be brought together to reduce the possibility of patient misalignment or they can be move apart to reduce the interference between the nuclear and MR scanners 12, 26 by moving one or both of the scanner 12, 26 along the tracks 94.

In radiation therapy planning, the patient must be in the same fixated position during the pre-treatments, between-treatments, and post-treatments image acquisitions as for during the radiation treatments procedure. Radiation treatment procedures in many cases include a series of planned (fractionated) dose deliveries. In one embodiment, the RTP couch or patient support 90 has substantially identical geometry to the tabletop of the radiation therapy system (not shown) which provides the radiation treatment to the subject. Typically this is a flat tabletop surface. Inaccuracies between the RTP couch 90 and the radiation therapy system tabletop geometries may result in poor patient position reproducibility, image spatial distortions, inaccurate patient markings, or the like which can potentially cause significant patient harm by causing inaccurate treatment with radiation. In another embodiment, the RTP couch 90 is detachable from the patient support track 92 for use in the radiation therapy system. By using the same couch for therapy planning and therapy delivery, image registration errors, positioning errors stemming from geometrical inaccuracies between the two couches are reduced or avoided.

A radiation treatment system tabletop is optionally larger than a conventional MR or nuclear imaging system patient support to accommodate various patient positions which aims to achieve an optimal treatment path to the target region. In either imaging system, the patient support and in some cases positioning/fixation of the patient with extremities elevated, is limited by the size of the bore, generally 60 cm for conventional MR systems and 70 cm for conventional PET systems, which in turn limits the available patient positions. This is one reason that radiation therapy planning is typically performed using computer tomography (CT) systems with larger bores (~80-85 cm) that can accept the larger radiation therapy couches. However, planning with CT systems is done at the cost of exposing already vulnerable patients to even more ionizing radiation which can have additional long term adverse side effects. Also, with additional ionizing radiation dose from CT there is a reluctance to perform intra-treatment imaging to assess treatment response or organ shift/changes for re-planning purposes. With MR this concern diminishes. However, CT is established for RTP since the attenuation properties of the tissue are directly obtained, hard tissue is imaged well and good geometric accuracy is achieved. With this in mind, an alternate embodiment includes large bore CT-MR combination for RTP. CT is presently the gold standard for RTP, but it is of medical benefit to have MR data to fuse with the CT data to improve the RT planning, to account for soft tissue structures or vessels near the tumor for example, as part of the treatment plan. Also, as mentioned, it is of benefit to use MR for tumor response monitoring/follow up due to the lack of additional ionizing radiation. Similar to the described large bore Nuclear Medicine (NM), e.g., PET, scanner and MR scanner, with RTP couch/flat tabletop, the NM scanner may instead be a large bore CT scanner. In this embodiment, a CT contrast agent replaces the PET contrast agent. In this way, a single workflow session for a given patient may be realized efficiently for RTP, where patient movement is minimized between the CT and MR image acquisitions with improved co-registration. Preferably the CT and MR scanners are in the same room. In an additional alternate embodiment, they are close spatially and the shared couch for RTP additionally includes a trolley that allows for easy transport of the fixated patient on flat tabletop, from one system to the other. In the described cases of CT+MR, CT may be used for RTP with MR data acquired and fused for improved planning, MR may be used for RTP, and either or both CT and MR may be used for treatment response/effectiveness monitoring (preferably MR). In another embodiment, a nuclear medicine scanner and a combined MR/CT scanner are provided. The NM and CT scanners can be used for planning and the NM and MR scanners can be used periodically for follow-up examinations to monitor progress.

The RTP system 10 includes the larger bores 16, 36, with a diameter of 70 cm or greater, and preferably 80-85 cm, which is large enough to accommodate the RTP couch 90 having dimensions replicating that of the corresponding radiation treatment system. In this arrangement, accurate patient positioning is reproduced between the RTP system 10 and the radiation treatment system to monitor treatment progress between fractions, or after several fractions, without introducing harmful additional ionizing radiation to the patient.

The RTP couch 90, and analogous treatment system couch, are flat rather than concave or curved such as in conventional imaging systems. Conventional imaging systems typically have a concave shape to conform to the circular opening of the bore and to limit the patient's movement. The vertical and longitudinal motion of the couch 90 is accurate and reproducible. The RTP couch 90 includes a plurality of the mounting structures 96, such as mounting holes, fixtures, or the like for accommodating various specialized attachments and restraints for precisely and repeatedly immobilizing the patient in a common, fixed position during the multiple fractions of a treatment cycle. The couch 90 and restraints are compatible for both MR imaging and nuclear and CT imaging and should not include any substantial artifact producing objects or materials. For example, the couch 90 is non-ferromagnetic, has low RF loss, and does not generate a proton signal to meet MR compatibility criteria. For nuclear and CT imaging compatibility, the couch 90 has low gamma ray and X-ray attenuation and scatter in the energy ranges used for imaging. These criteria for MR can generally be achieved with mechanical design, glass and/or kevlar reinforced plastics, with some degree of gamma ray and X-ray attenuation, which for nuclear and CT imaging compatibility can be modeled and quantified for the RTP couch 90 and MR coil or patient fixation accessories, and accounted for by the respective reconstruction processors 50, 66.

Registration marks, fiducial markers, 98 in FIG. 1, or a combination of the two are incorporated into or on the surface of the couch 90 which registers the couch relative to the image scanners 12, 26 and the subject. In one embodiment, a patient registration system 100 detects the registration marks, e.g. grids, lines, points, or the like, or the fiducial markers 98. The patient registration system 100 includes at least one of a gantry laser 102, a wall mounted laser (not shown), an overhead (not shown), or any combination thereof which have precise spatial relationships to the isocenter of the two examination regions 18, 36. The lasers generate a signal representative of the three dimensional (3D) spatial position of the registration marks according to the laser angle and measured distance relative to the examination regions 18, 36. A registration processor 104 determines the three dimensional spatial coordinates of the registration marks according to these signals and compares the actual coordinate position of the registration marks to the expected coordinate position. The patient can be tattooed with registration marks which are then detectable by the patient registration system 100 for localization. The registration processor 104 determines the comparison between the actual coordinate position, received from the registration system 100, and the expected coordinate position of the registration marks and generates a feedback signal which is displayed on the GUI 80 for advising a clinician. A similar feedback signal is generated by the registration processor 104 for registering the RTP couch 90 to the corresponding examination region 18, 36. The generated signal instructs the controller 40, 60 of each respective imaging scanner 12, 26 to adjust the vertical and/or horizontal position of the RTP couch 90 accordingly.

In another embodiment, fiducial markers, which are imageable by the both scanners 12, 26, are affixed to the mounting structures 96 of the RTP couch 90 and/or the patient, or to fixation devices attached to the patient. Localization scans are performed to determine the 3D coordinate positions of the fiducial markers relative to the imaging region 18, 36. The registration processor 104 determines the actual coordinate positions of the fiducials from the localization scans and compares them to the expected coordinate positions. The registration processor 104 instructs the clinician via the GUI 80 to reposition the patient or instructs the respective scanner controllers to reposition the RTP couch 90. It should be appreciated that the fiducial markers can be detectable by the patient registration system 100 such that the patient and the couch 90 can be registered using either the imaging scanners 12, 26 or the patient registration system 100 with the fiducial markers. The fiducial markers may be visible in the individual modality image data sets to ease the registration of multiple modality image data sets for a fused image display for RTP and treatment monitoring. In a preferred workflow for monitoring, the patient returns for scanning, their fixation and fiducial marker arrangement is applied, and the newly acquired image data are optionally (and automatically) fused with the image data pre-treatment.

Figure 2:
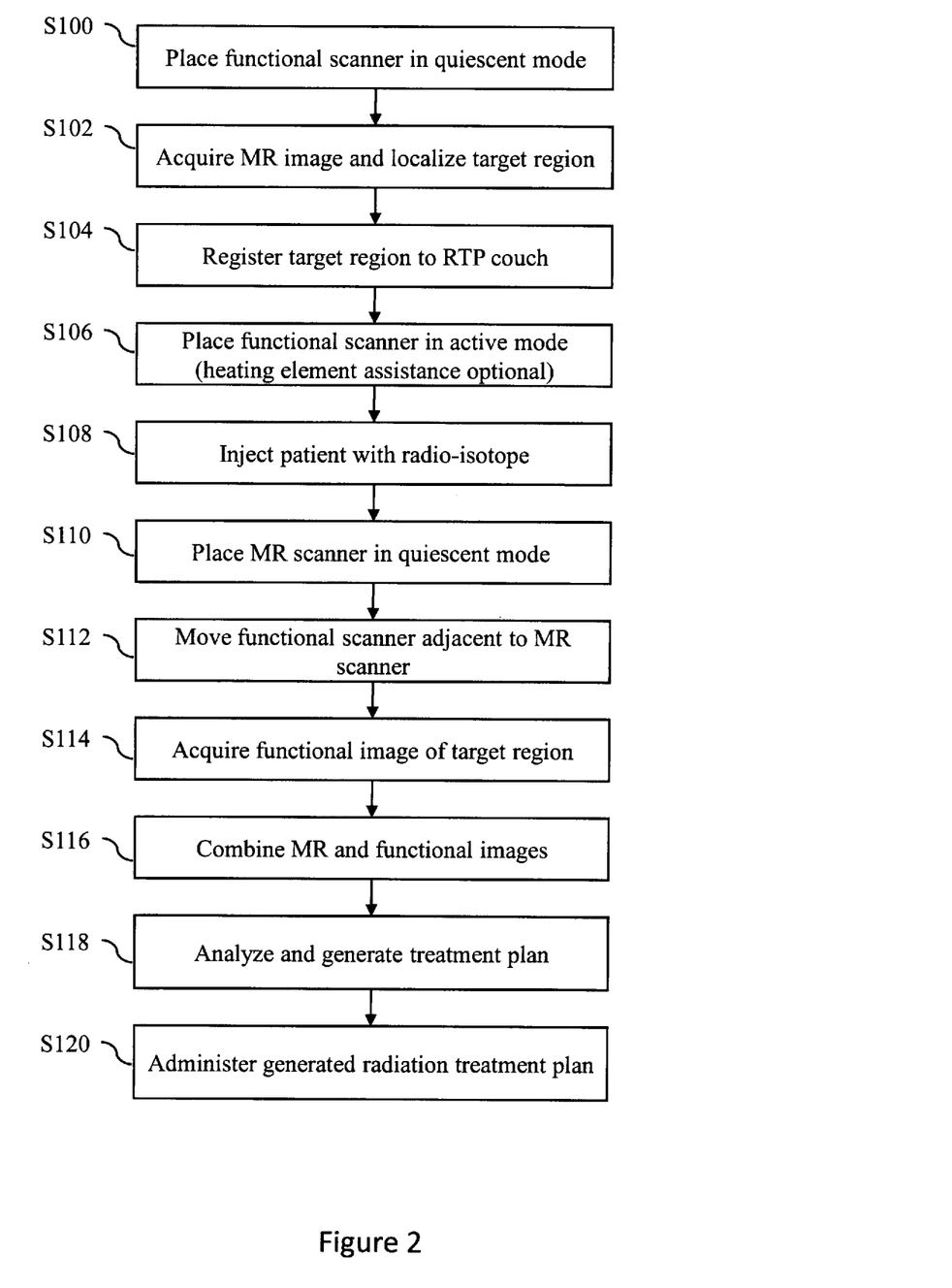
FIG. 2 is a flow chart of a method of planning radiation therapy with the system of FIG. 1.

With reference to FIG. 2, in pre-treatment radiation therapy planning, the target volume, which is to receive therapeutic radiation doses, is imaged then localized S102 relative to the MR imaging region 18 using the MR scanner 12 after the nuclear scanner 26 is place in a quiescent mode S100. The quiescent mode refers to an operating mode in which the scanner does not emit any noise, e.g. electrical or RF, that can potentially cause interference with the functioning of the other scanner. MR imaging of the target region generates anatomical data regarding the shape, size and position for the target region. MR imaging is superior to CT imaging for delineating tumor soft tissue versus healthy tissue as well as surrounding soft tissue or vessel structures. CT is superior to MR imaging for imaging of harder tissues, including bone, and also remains preferred in some conditions for very fast scanning in certain body applications where motion artifacts due to breathing affect image quality. Once the target region is localized, the patient position and the target volume are registered to the RTP couch S104 using the patient registration system 100. The registration process determines the expected coordinate position of the registration marks on the patient and the RTP couch 90. The nuclear scanner 26 is placed in an active mode S106 with the optional aid of the heating element 72. To prepare for nuclear image data acquisition, the patient is injected, or was previously injected prior to the start of the MR study, with a radio-isotope S108. The MR scanner 12 is placed in a quiescent mode S110 and the nuclear scanner 26 is optionally moved adjacent to the MR scanner S112 to reduce the longitudinal distance the patient travels between the MR and the nuclear imaging regions 18, 36. The MR scanner is placed in a quiescent mode during the acquisition of a pre-treatment nuclear image representation of the target region S114. Nuclear imaging, such as PET, offers functional data rather than anatomical data of the target region, such as characterizing cell proliferation to show presence of tumors, blood flow, cell necrosis, hypoxia, or the like of the target region. The functional data can be useful for updating a generated treatment plan during the treatment cycle to account for increases or decreases in tumor malignancy, cell death, or other clinically significant findings. The registered pre-treatment image representations from the MR and PET scanners 12, 26 are combined S116 into a composite image by a fusion processor 110. The fused image is analyzed by a planning processor 112 which generates or updates a treatment plan S118 according to the anatomical and functional characteristics of the target region. The generated or updated radiation treatment plan from S118 is carried out by a separate radiation treatment system according to the generated or updated treatment plan S120 such that the patient is positioned on a treatment couch, of the radiation treatment system, according to the determined expected coordinate position. In another embodiment, the fixated patient is transported from the RTP system 10 to the radiation treatment system on a trolley such that the patient is imaged and treated on the same RTP couch 90. The treatment plan is of course overseen, adjusted and approved by a treatment specialist, such as a radiation oncologist. Visualization of the treatment plan may be on the graphical user interface (GUI) 80 or on a separate Treatment Planning GUI (not shown) interfaced to the planning processor 112.

Figure 3:
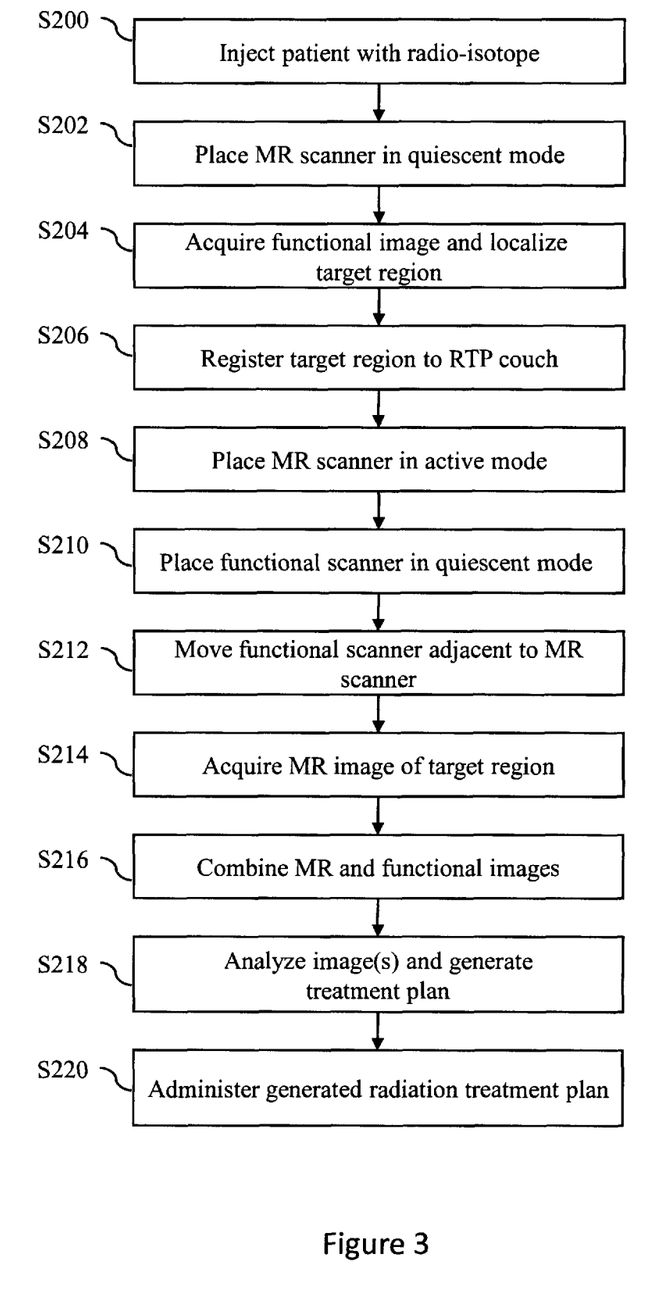
FIG. 3 is a flow chart of another method of planning radiation therapy with the system of FIG. 1.

With reference to FIG. 3, to prepare for nuclear image data acquisition, the patient is injected, or was previously injected prior to the start of the MR study, with a radio-isotope S200 and the MR scanner 12 is place in a quiescent mode S202. The target volume, which is to receive therapeutic radiation doses, is then imaged and localized S204 relative to the nuclear imaging region 36 using the nuclear scanner 26. Nuclear imaging of the target region generates functional data regarding the characterization of cell proliferation to show presence of tumors, blood flow, cell necrosis, hypoxia, or the like of the target region. The functional data can be useful for updating a generated treatment plan during the treatment cycle to account for increases or decreases in malignancy or cell death. Once the target region is localized, the patient position and the target volume are registered to the RTP couch S206 using the patient registration system 100. The registration process determines the expected coordinate position of the registration marks on the patient and the RTP couch 90. The MR scanner 12 is placed in an active mode S208 while to nuclear scanner 26 is placed in a quiescent mode S210 and is optionally moved adjacent S212 to the MR scanner 12 to reduce the longitudinal distance the patient travels between the MR and the nuclear imaging regions 18, 36. MR imaging of the target region generates anatomical data regarding the shape, size and position for the target region rather than functional data. MR imaging is superior to CT imaging for delineating tumor soft tissue versus health tissue. As well as surrounding soft tissue or vessel structures. CT is superior to MR imaging for imaging of harder tissues, including bone, and also remains preferred in some conditions for very fast scanning in certain body applications where motion artifacts due to breathing affect image quality. After MR image data acquisition S214, the registered pre-treatment image representations from the MR and nuclear scanners 12, 26 are combined S216 into a composite image by a fusion processor 110. The fused image is analyzed by a planning processor 112 which generates or updates a treatment plan S218 according to the anatomical and functional characteristics of the target region. The radiation treatment is carried out by a radiation treatment system according to generated or updated treatment plan S220 such that the patient is positioned on a treatment couch, of the radiation treatment system, according to the determined expected coordinate position. The treatment plan is of course overseen, adjusted and approved by a treatment specialist, such as a radiation oncologist. Visualization of the treatment plan may be on the graphical user interface (GUI) 80 or on a separate Treatment Planning GUI (not shown) interfaced to the planning processor 112.

Although described above with the anatomical images being taken prior to the functional images, it is to be appreciated that the order can be reversed.

Figure 4:
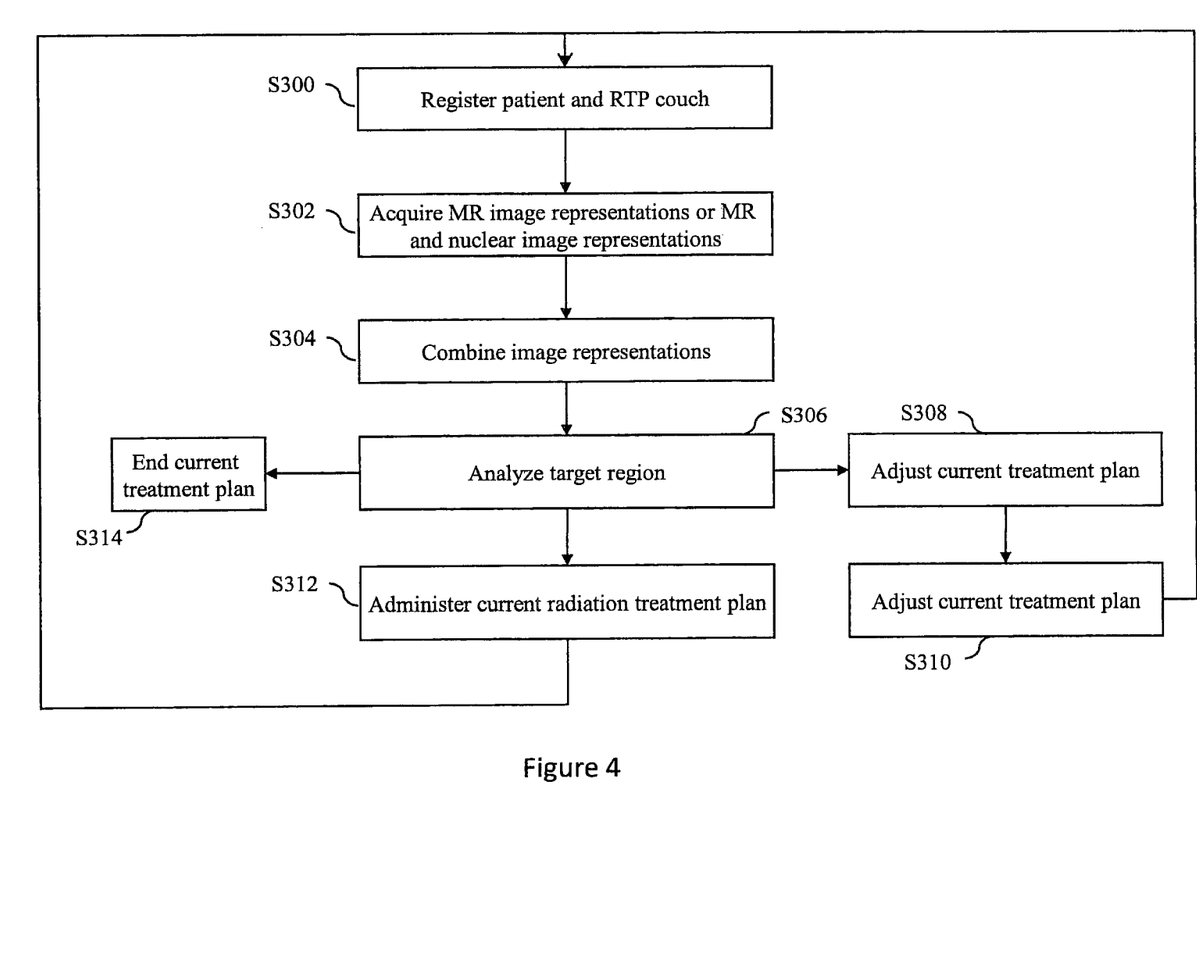
FIG. 4 is a flow chart of a method of monitoring and updating radiation therapy with the system of FIG. 1.

With reference to FIG. 4, since the patient is not subjected to the harmful additional ionizing radiation of CT imaging, intra-treatment MR, or MR and NM, imaging and monitoring can be performed more often, such as before and after each treatment session. After the patient and the RTP couch 90 are registered S300 according to the expected coordinate position of the patient during the planning process, MR and nuclear images of the target region are acquired S302 and combined S304 with the fusion processor 112. The planning processor 112 analyzes the fused mage representation S306 and determines whether to update the current treatment plan S308 and administer the updated treatment plan S310, continue with the current treatment plan and administer the treatment fraction again S312, or to end the treatment cycle S314 because the target volume has been eradicated or is no long malignant. In some cases only MR data may be acquired for the treatment monitoring phase.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A radiation therapy planning and follow-up system, comprising:
   a magnetic resonance (MR) scanner with a first bore which defines an MR imaging region configured to receive a subject along an MR longitudinal axis;
   a second imaging scanner with a second bore which defines a second imaging region configured to receive the subject along a second longitudinal axis, the second longitudinal axis being aligned with the MR longitudinal axis; and
   a radiation therapy type couch configured to move linearly through the MR and second imaging regions and configured to position the subject sequentially in the MR and second imaging regions, the radiation therapy type couch including a tabletop surface and mounting structures configured to accept restraint device which reproducibly constrain a subject in a selected, fixed position with an extremity elevated;
   wherein the first and second bores have a diameter of at least 70 cm to accommodate a subject constrained on the tabletop surface with the elevated extremity;
   a plurality of registration marks disposed at least one of on the flat tabletop surface, incorporated in the radiation therapy type couch, on the restraint devices or on the subject;
   a registration system configured to determine the location of the registration marks in three dimensions with the subject in each of the first bore and the second bore and generate a feedback signal which instructs at least one of an MR scan controller and a second imaging scanner scan controller to adjust a position of the radiation therapy type couch and/or slice or slab positions for aligned image acquisition;
   a fusion processor configured to combine an image representation generated from data collection in the MR imaging region and an image representation generated from data collection in the second imaging region into a composite image representation; and
   a planning processor configured to generate a radiation therapy treatment plan according to the composite image;
   wherein the second scanner includes a PET scanner, the PET scanner with a PET bore which defines a PET imaging region including:
      a ring of optical detectors dispose adjacent to the PET imaging region optical coupled to a scintillator layer, the ring of optical detectors being configured to generate nuclear imaging data in response to emitted radiation in the PET imaging region; and
      a heater configured to heat the scintillator; and
      a controller configured to place the PET scanner in a quiescent mode in which the PET scanner does not emit electrical or RF noise during MR imaging and returns the PET scanner to an active mode after the MR imaging including controlling the heater to heat the scintillator layer to an operating temperature.

2. The radiation therapy planning and follow-up system according to claim 1, wherein the patient registration system includes:
   at least one laser having a precise relationship to an isocenter of the MR and second imaging regions and configured to generate a signal representative of a location of each of a plurality registration marks disposed on the subject, on fixation devices attached to the patient, and/or the radiation therapy couch; and
   a registration processor configured to determine a three-dimensional coordinate position of each registration mark according to the generated signal.

3. The radiation therapy planning and follow-up system according to claim 2, wherein the second scanner is a nuclear scanner and the registration processor is configured to generate a feedback signal based on an actual coordinate position and an expected coordinate position of each registration mark and at least one of:
   displays the generated feedback signal on a graphical user interface;
   instructs at least one of a MR scan controller and a nuclear scan controller to adjust the position of the radiation therapy couch and/or the slice or slab positions for image acquisition; and
   provides the feedback signal to a fusion processor configured to combine the nuclear and MR image representations.

4. A radiation therapy planning and follow-up system comprising:
   a magnetic resonance (MR) scanner with a first bore which defines an MR imaging region configured to receive a subject along an MR longitudinal axis, the first bore having a diameter of at least 70 cm;
   a second imaging scanner with a second bore which defines a second imaging region configured to receive the subject along a second longitudinal axis, the second longitudinal axis being aligned with the MR longitudinal axis and the second bore having a diameter at least 70 cm;
   a radiation therapy type couch configured to move linearly through the MR and second imaging regions and configured to position the subject sequentially in the MR and second imaging regions, the radiation therapy type couch including a flat tabletop surface and mounting structures configured to accept restraint devices which reproducibly constrain a subject in a selected, fixed position with an extremity elevated;
   wherein the second scanner includes a PET scanner, the PET scanner with a PET bore which defines a PET imaging region including:
      a ring of optical detectors dispose adjacent to the PET imaging region optical coupled to a scintillator layer, the ring of optical detectors being configured to generate nuclear imaging data in response to emitted radiation in the PET imaging region;
      a radio-frequency shield disposed between the scintillator layer and the PET imaging region and configured to shield the MR scanner from radio frequency noise emanating from the PET scanner;
      a heating element adjacent to the optical detectors configured to heat the optical detectors and associated circuitry;
      one or more circuits configured to temporarily lower an operating voltage in photo-multiplier tube optical detectors to place the PET scanner in a quiescent state in which the PET scanner emits a reduced amount of the radio frequency noise when the MR scanner is generating image data and to control the operating voltage and control the heating element to raise the optical detector to a nominal operating temperature to place the PET scanner in an active state to prepare the PET scanner to generate image data.

5. The radiation therapy planning and follow-up system according to claim 1, wherein the radiation therapy planning and follow-up system is disposed on a mobile platform configured to be transported from one location to another.

6. A method for generating or updating a radiation therapy plan, comprising:
with an MR scanner or a second scanner, acquiring an MR or second image representation of a target volume supported on a flat radiation therapy couch in one of an MR imaging region of the MR scanner and a second imaging region of the second scanner, and localizing the target volume relative to the corresponding imaging region, the radiation therapy type couch including a flat tabletop surface and mounting structures configured to accept restraint device which reproducibly constrain a subject in a selected, fixed position with an extremity elevated;
with one or more computers, registering the localized target volume to the flat radiation therapy couch and determining an expected coordinate position of the target volume relative to the flat radiation therapy couch;
with guide rails, re-positioning the flat radiation therapy couch linearly from one of the MR imaging region and second imaging region to the other imaging region of the second scanner and MR scanner which shares a common longitudinal axis therewith;
acquiring an image representation of the target volume with the other one of the second and MR scanners;
with the one or more computers, combining the MR and second image representations in a combined image representation; and
with the one or more computers, generating or updating a radiation therapy plan for treating the target volume with ionizing radiation according to the acquired MR and second image representations,
wherein a first bore which defines the MR imaging region and a second bore which defines the second imaging region each have a diameter of at least 70 cm to accommodate the flat radiation therapy couch with the subject with the extremity elevated,
wherein the second scanner includes a PET scanner including a scintillator layer and a ring of optical detectors optically coupled to the scintillator layer and further including:
prior to acquiring the MR image representation, placing the PET scanner in a quiescent mode;
while the PET scanner is in the quiescent mode, maintaining a minimum operating temperature of the optical detectors of the PET scanner,
after acquiring the MR image representation, placing the PET scanner in an active mode; and
while placing the PET scanner in the active mode, heating the optical detectors of the nuclear scanner with a heating device to a nominal operating temperature.

7. The method according to claim 6, further including:
transporting the flat radiation therapy couch with an immobilized subject thereon to a radiation treatment system; and
with the radiation treatment system, administering ionizing radiation according to the generated or updated radiation therapy plan.

8. The method according to claim 7, further including after administering ionizing radiation according to the generated or updated radiation therapy plan, repeating the method steps of:
with the MR scanner or the second scanner, acquiring another MR or second image representation of a target volume, and localizing the target volume of the another MR or second image representation relative to the corresponding imaging region;
with the one or more computers, registering the localized target volume of the another MR second image representation to the flat radiation therapy couch and determining an expected coordinate position of the target volume relative to the radiation therapy couch;
with the guide rails, re-positioning the flat radiation therapy couch linearly from one of the MR imaging region and second imaging region to the other imaging region of the second scanner and MR scanner;
acquiring an image representation of the target volume with the other one of the second and MR scanners;
with the one or more computers combining the another MR and second image representations in a combined current image representation; and
updating the radiation therapy plan according to the current combined image representation.

9. The method according to claim 6, further including:
prior to acquiring a PET image representation, placing the MR scanner in a quiescent mode; and
after acquiring the PET image representation, placing the MR scanner in an active mode.

10. The method according to claim 9, wherein the second scanner includes a nuclear scanner and further including:
shielding optical detectors and electronics of the nuclear scanner from RF and static magnetic field interference from the MR scanner.

11. The method according to claim 10, further including:
shielding the MR scanner from RF noise emitted by the nuclear scanner.

12. The method according to claim 7, wherein repositioning the flat radiation therapy couch between the MR imaging region and the second imaging region includes moving the flat radiation therapy couch linearly along rails and further including:
prior to transporting the flat radiation therapy couch to the radiation treatment system, detaching the radiation therapy couch from the rails.

* * * * *